(12) United States Patent
Ryu

(10) Patent No.: US 10,208,329 B2
(45) Date of Patent: Feb. 19, 2019

(54) DEVICE FOR MEASURING ANTIMICROBIAL ACTIVITY OF GAS AND METHOD FOR MEASURING ANTIMICROBIAL ACTIVITY OF GAS

(71) Applicant: Korea University Research and Business Foundation, Seoul (KR)

(72) Inventor: Jee-Hoon Ryu, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 177 days.

(21) Appl. No.: 15/125,400

(22) PCT Filed: Feb. 4, 2015

(86) PCT No.: PCT/KR2015/001127
§ 371 (c)(1),
(2) Date: Sep. 12, 2016

(87) PCT Pub. No.: WO2015/137625
PCT Pub. Date: Sep. 17, 2015

(65) Prior Publication Data
US 2017/0073726 A1     Mar. 16, 2017

(30) Foreign Application Priority Data

Mar. 13, 2014   (KR) .................. 10-2014-0029504

(51) Int. Cl.
*C12M 1/00*      (2006.01)
*C12Q 1/18*      (2006.01)
*G01N 21/80*     (2006.01)

(52) U.S. Cl.
CPC ............. *C12Q 1/18* (2013.01); *G01N 21/80* (2013.01)

(58) Field of Classification Search
CPC .......................... C12M 23/34; C12M 23/36
See application file for complete search history.

(56) References Cited

FOREIGN PATENT DOCUMENTS

| JP | 0002562221 A | 11/1990 |
| JP | 2001213701 A | 1/2000 |
| KR | 20020033080 A | 10/2001 |
| KR | 20040098043 A | 10/2004 |

OTHER PUBLICATIONS

Google Patents English machine translation of Ekika Tansan KK, JP 2001-213701 A.*
Becerril et al., "Combination of analytical and microbiological techniques to study the antimicrobial activity of a new active food packaging containing cinnamon or oregano against *E. coli* and *S. aureus*," Anal Bioanal Chem 388:1003-1011, 2007.*

\* cited by examiner

*Primary Examiner* — Rosanne Kosson
(74) *Attorney, Agent, or Firm* — Fox Rothschild LLP

(57) ABSTRACT

The present invention relates to a device for measuring the antimicrobial activity of a gas and a method for measuring the antimicrobial activity of a gas. The present invention can be used as a standardized device for measuring the antimicrobial activity of a gas or as a standardized method for measuring the antimicrobial activity of a gas as the present invention is capable of constantly maintaining the concentration of a gas and identifying the growth and development of microorganisms objectively through a color change of a microorganism culture medium containing a pH indicator.

19 Claims, 23 Drawing Sheets

[Fig. 1a]
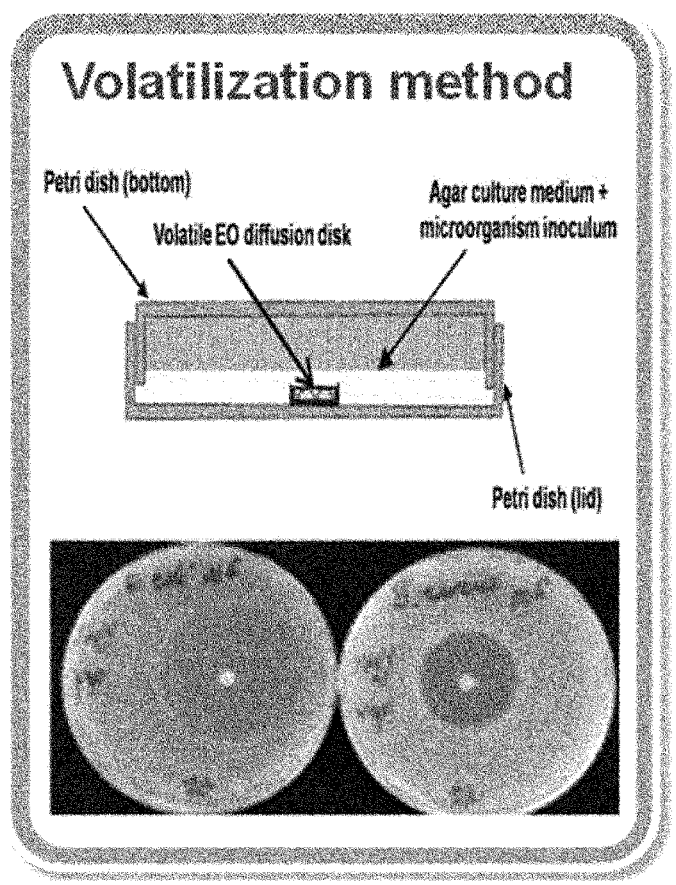

[Fig. 1b]
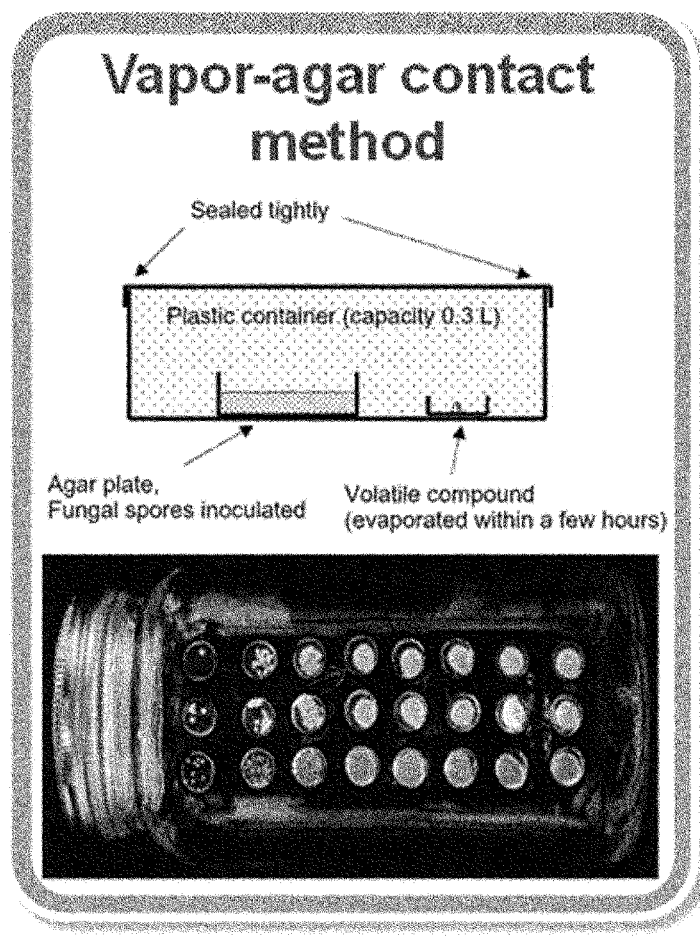

[Fig. 1c]
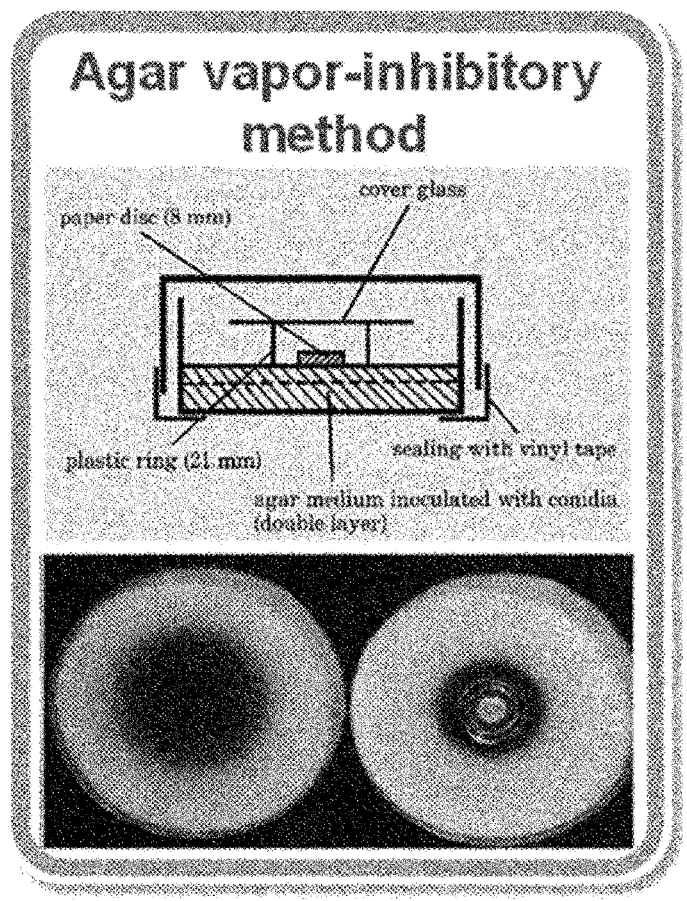
[Fig. 2a]
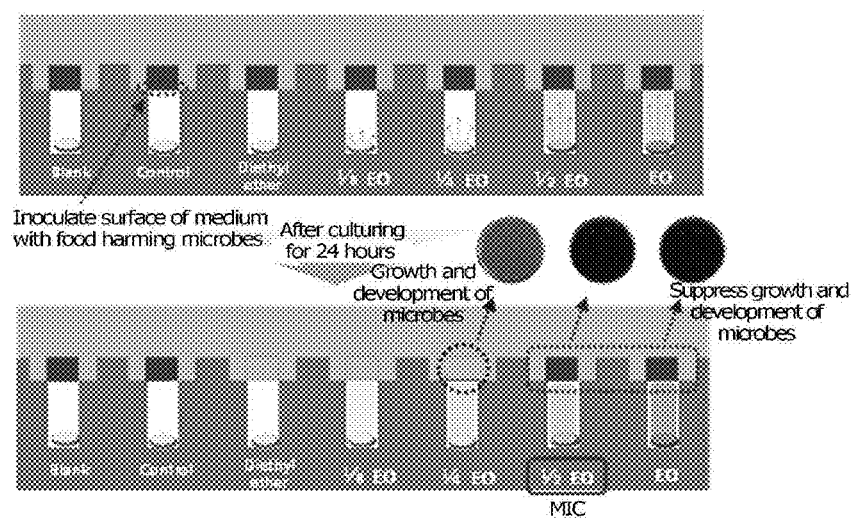

[Fig. 2b]
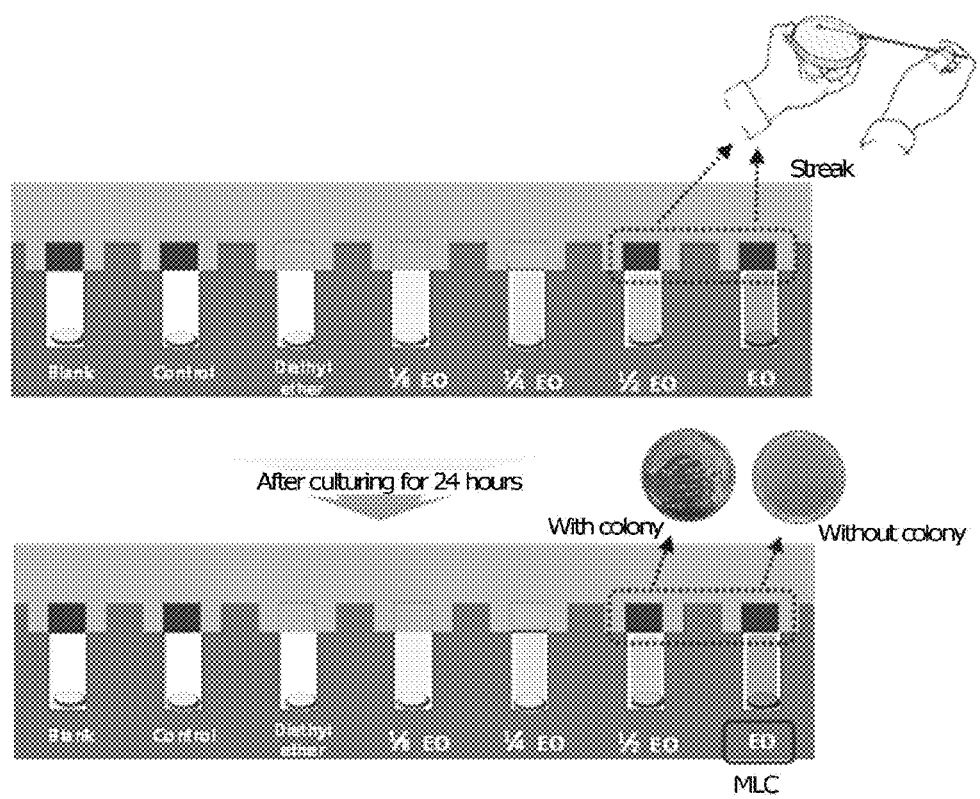

[Fig. 3a]
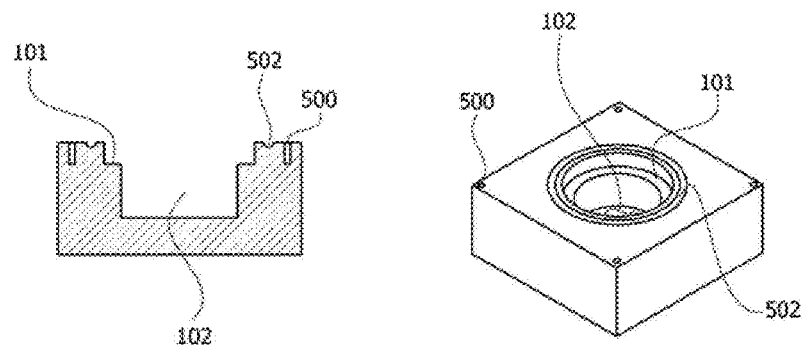
[Fig. 3b]
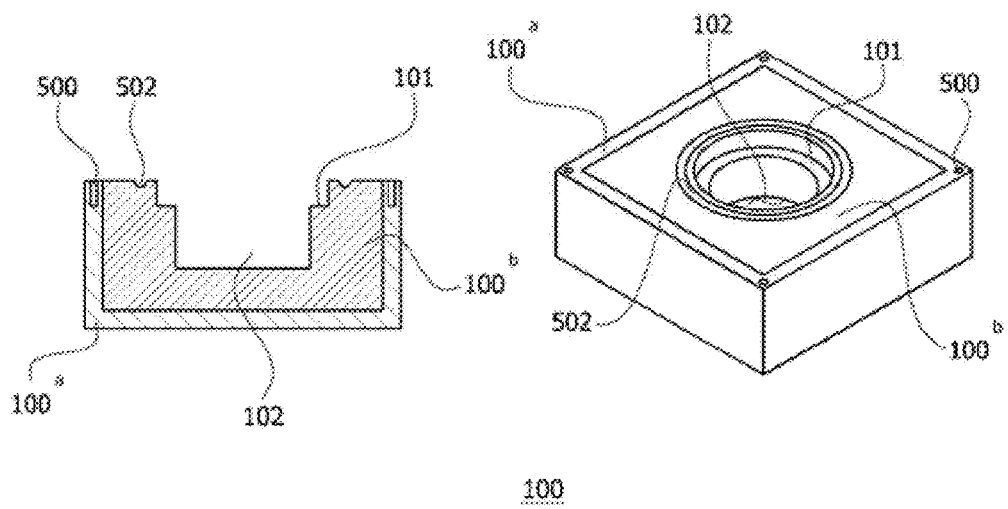

[Fig. 3c]
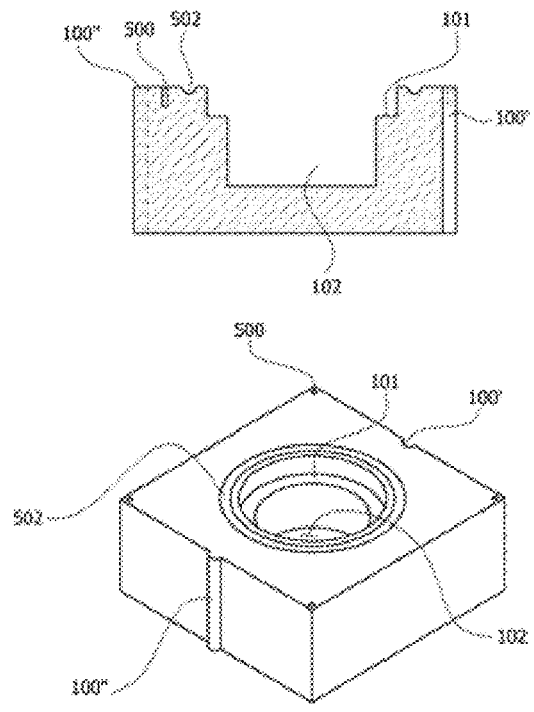
[Fig. 3d]
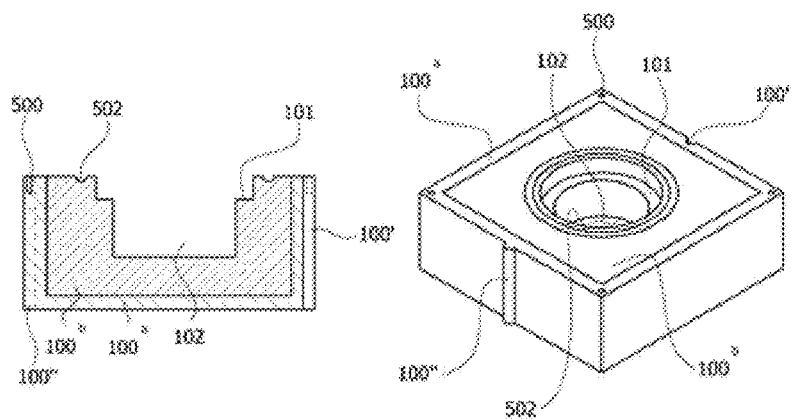

[Fig. 3e]
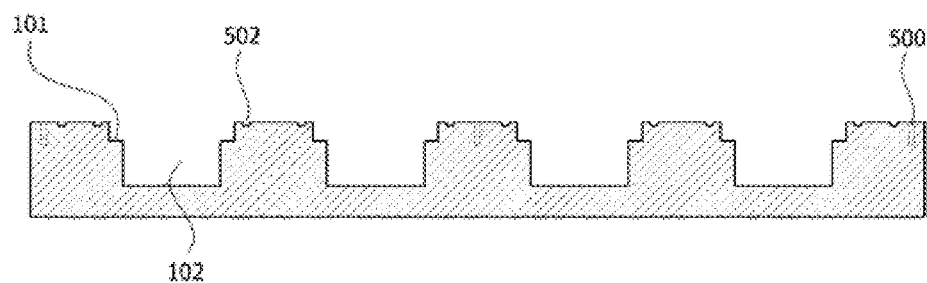
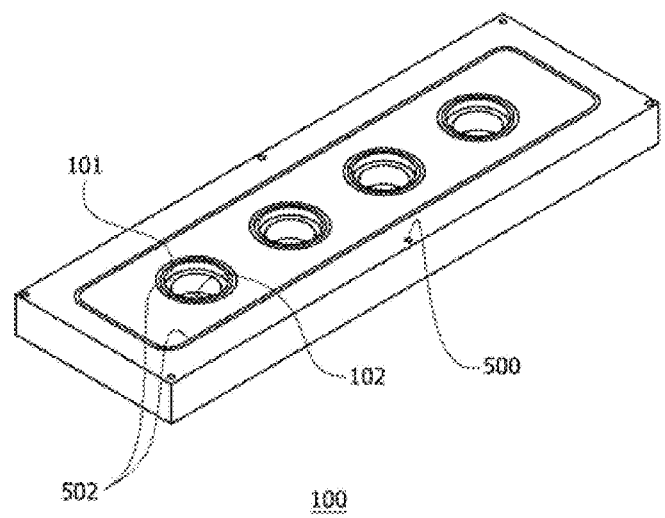

[Fig. 3f]
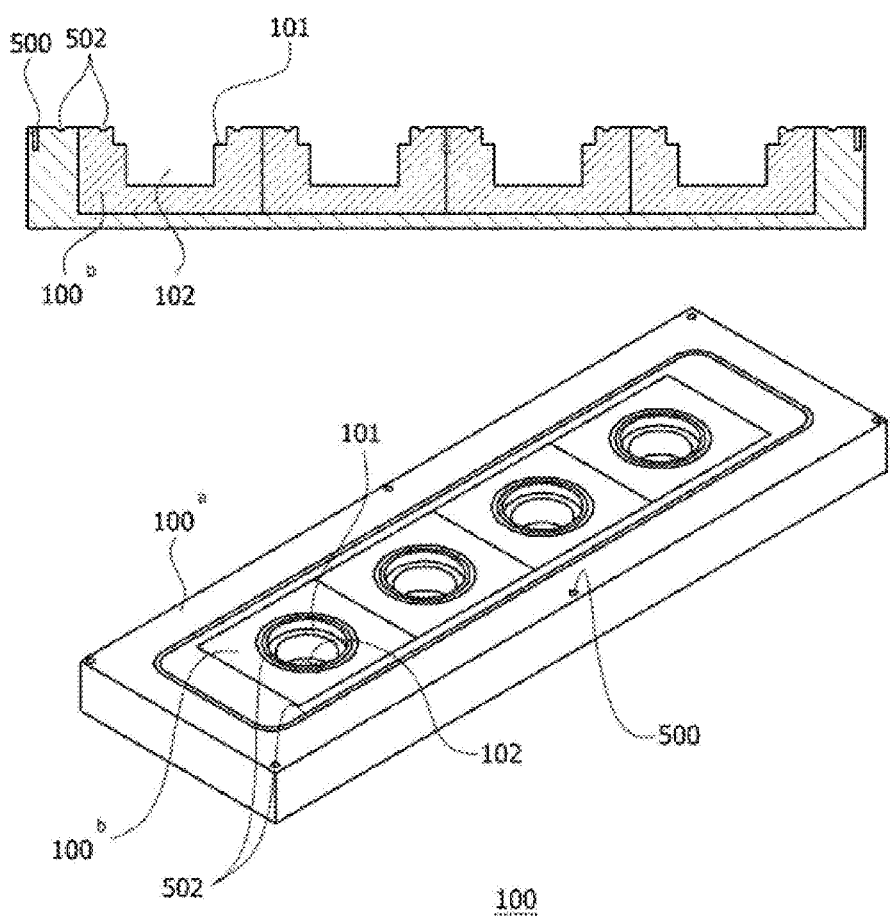

[Fig. 3g]
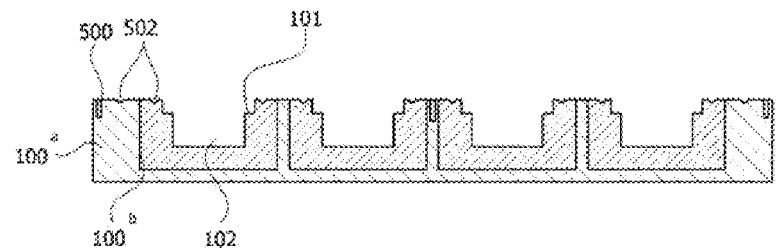
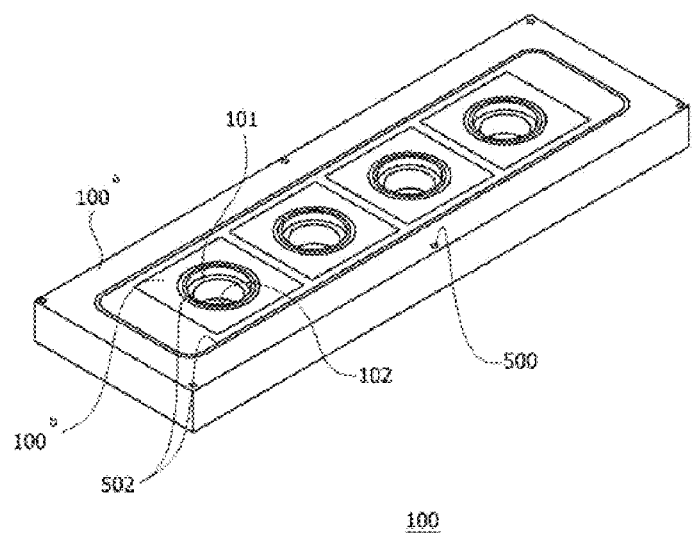
[Fig. 4a]
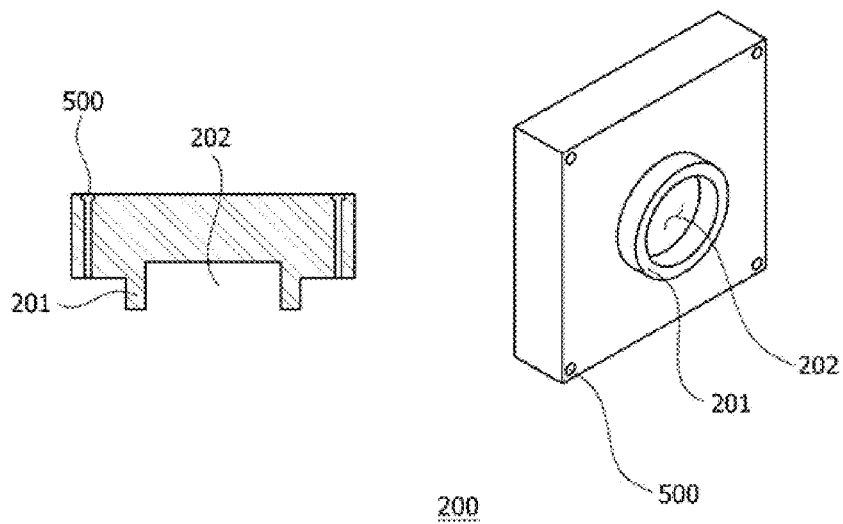

[Fig. 4b]
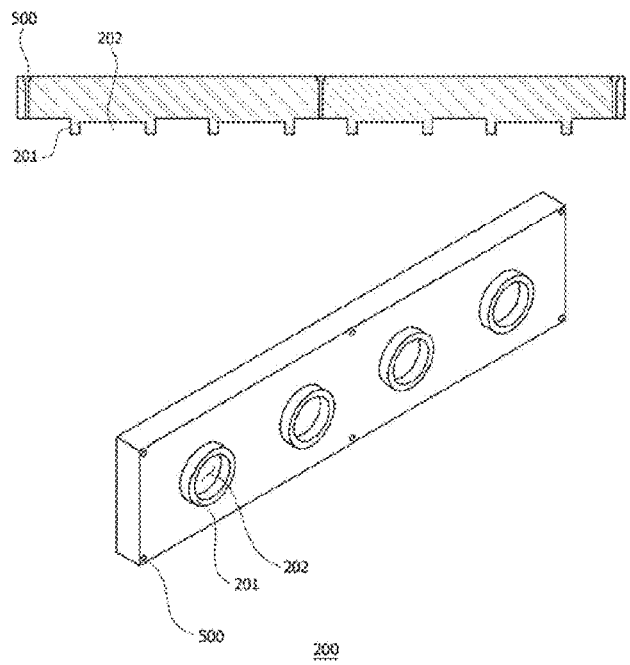
[Fig. 4c]
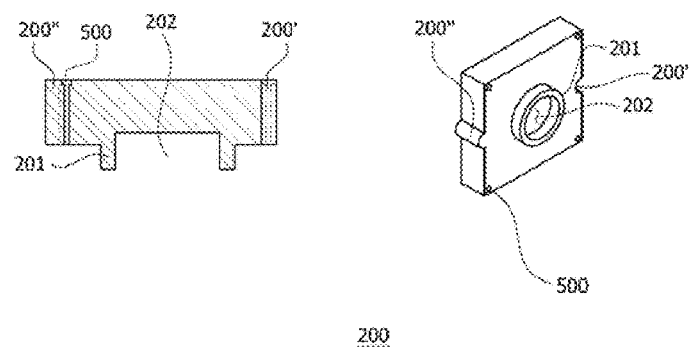
[Fig. 5a]
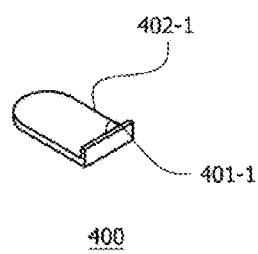

[Fig. 5b]
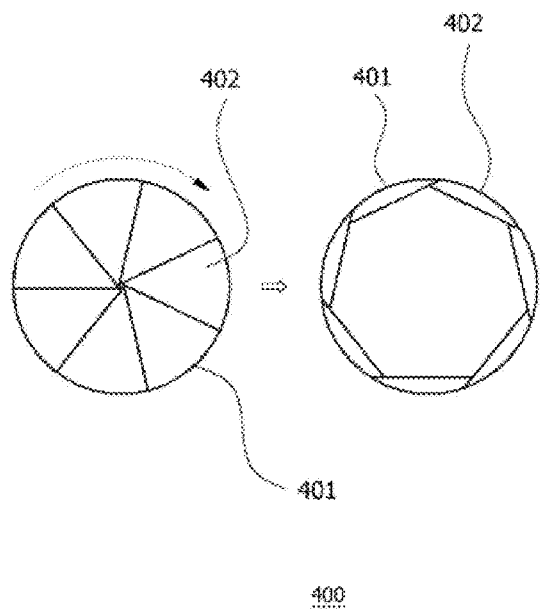
[Fig. 6a]
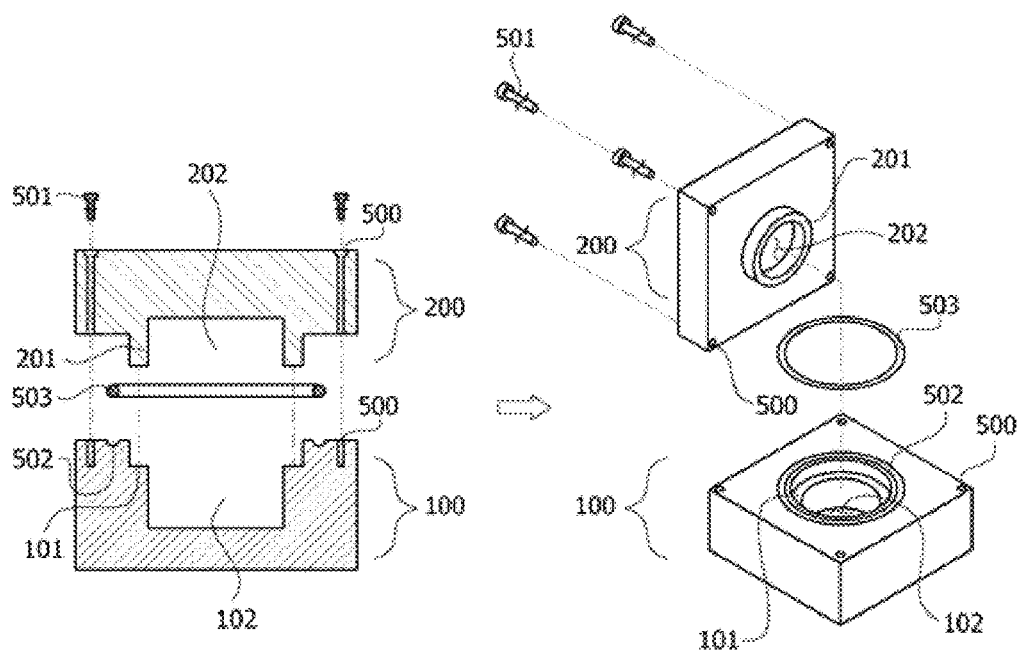

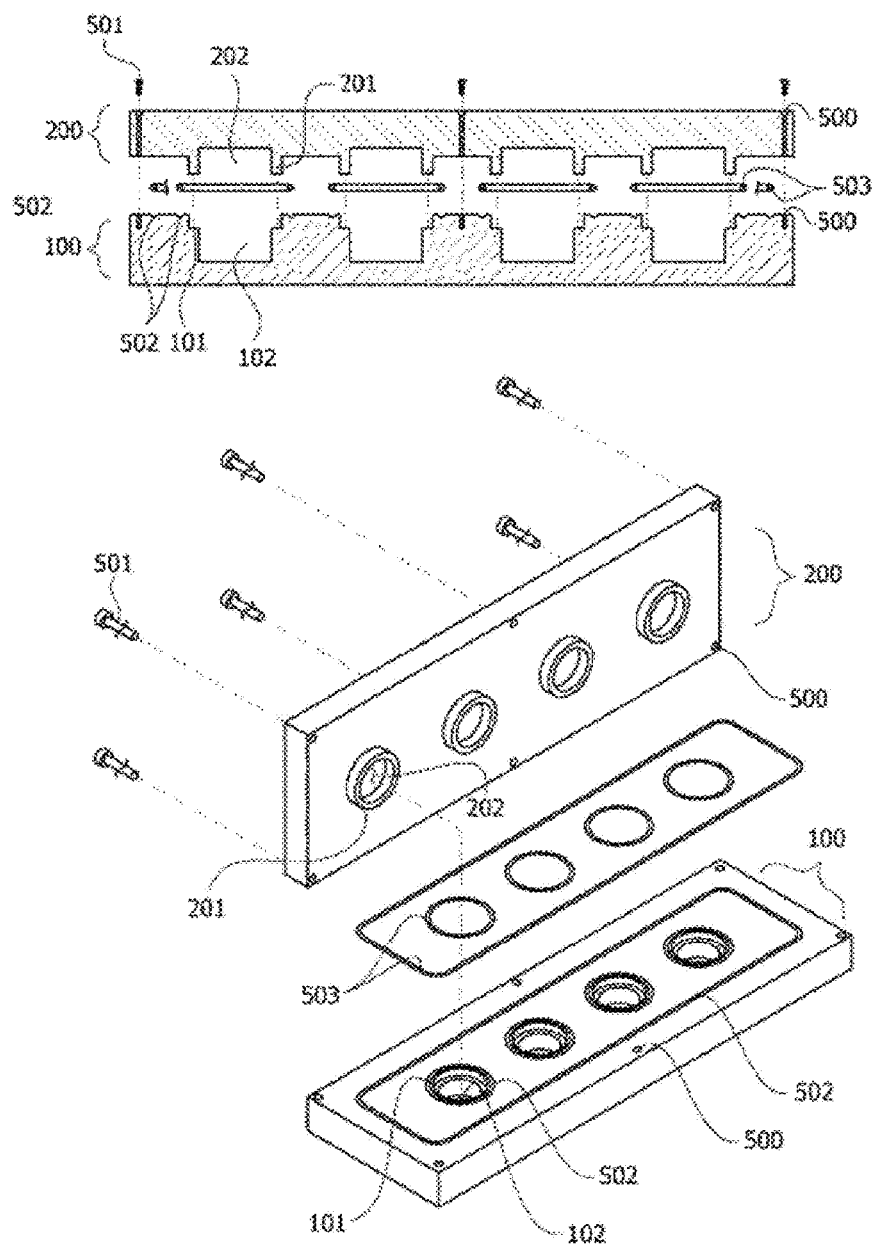
[Fig. 6b]

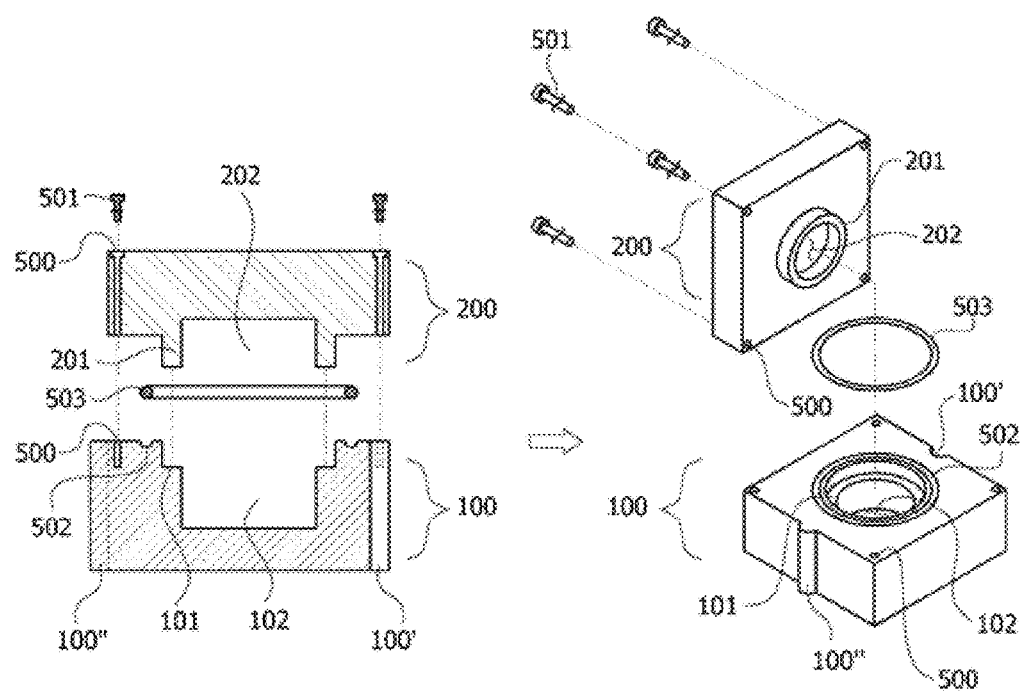
[Fig. 6c]

[Fig. 6d]
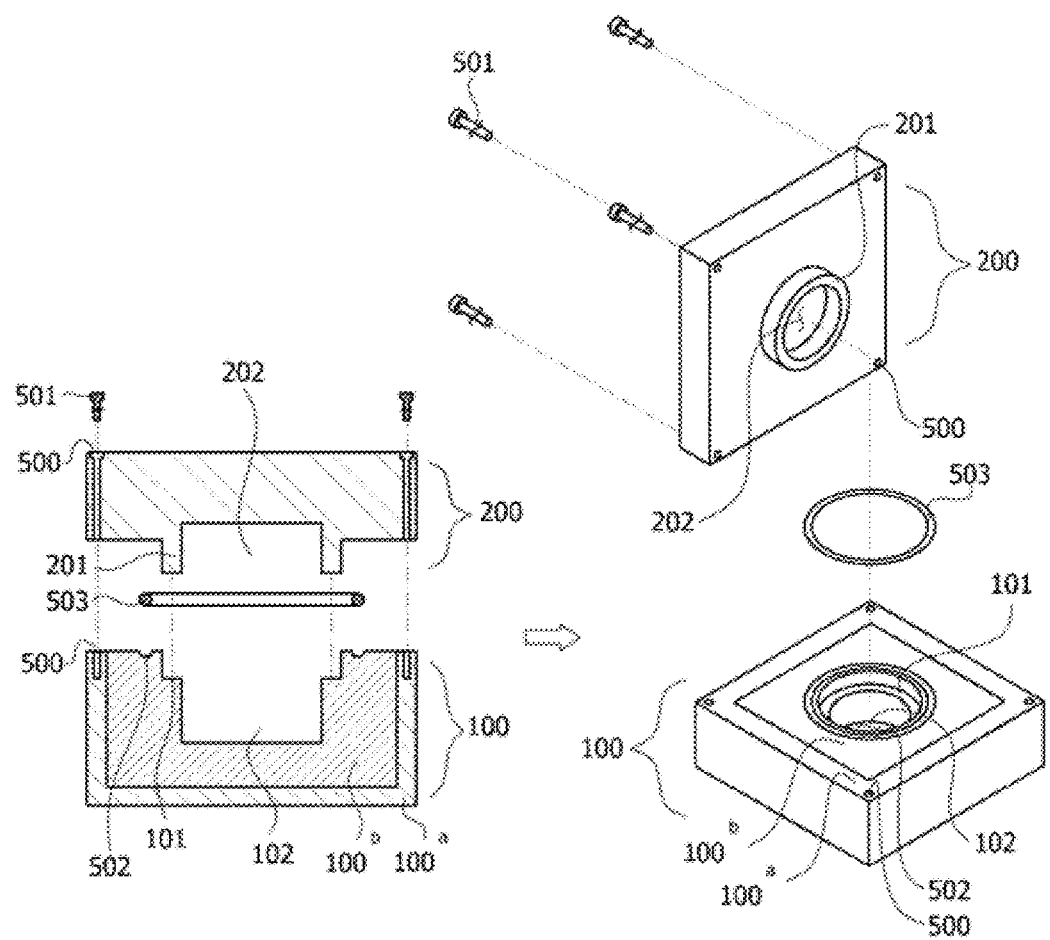

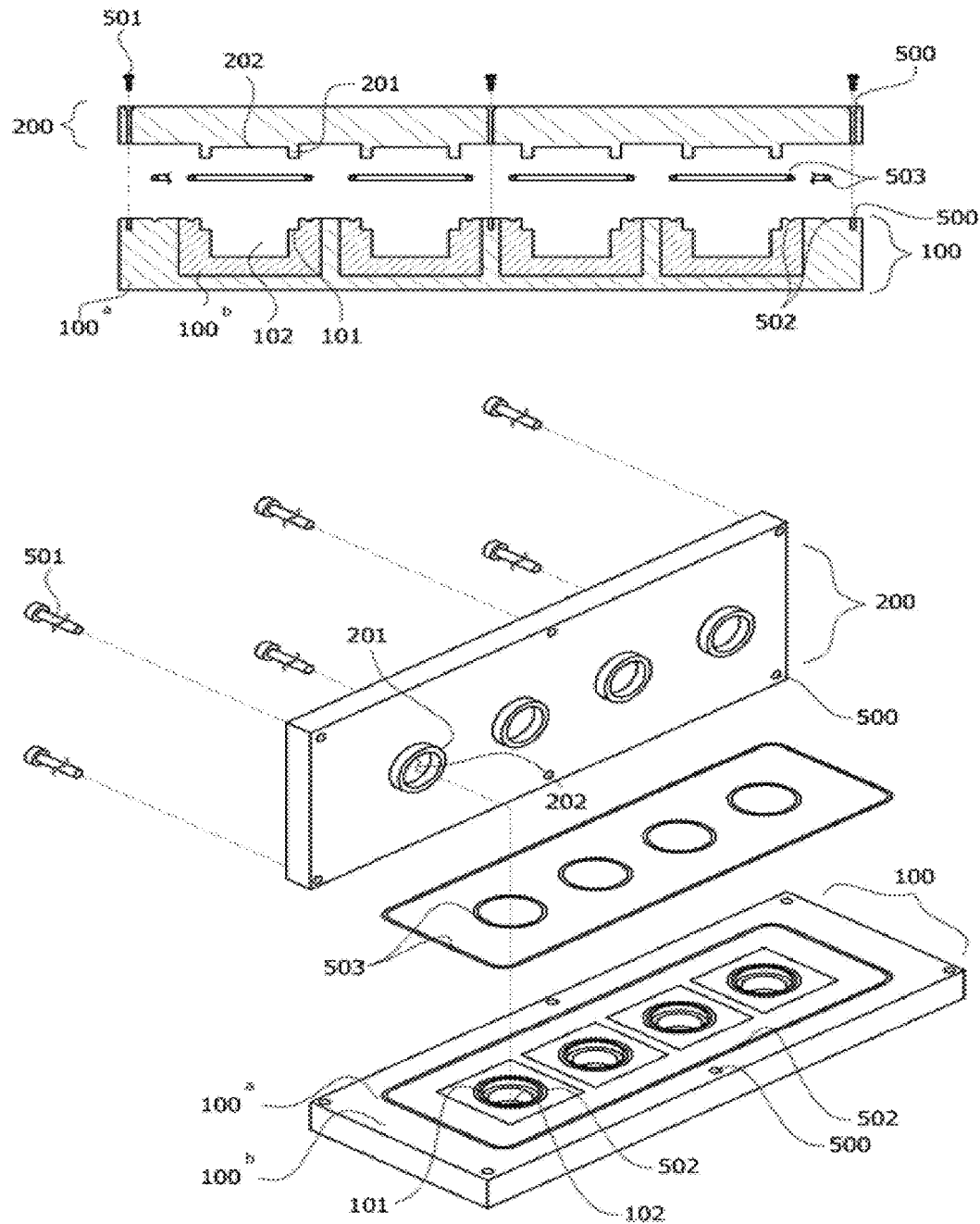
[Fig. 6e]

[Fig. 6f]
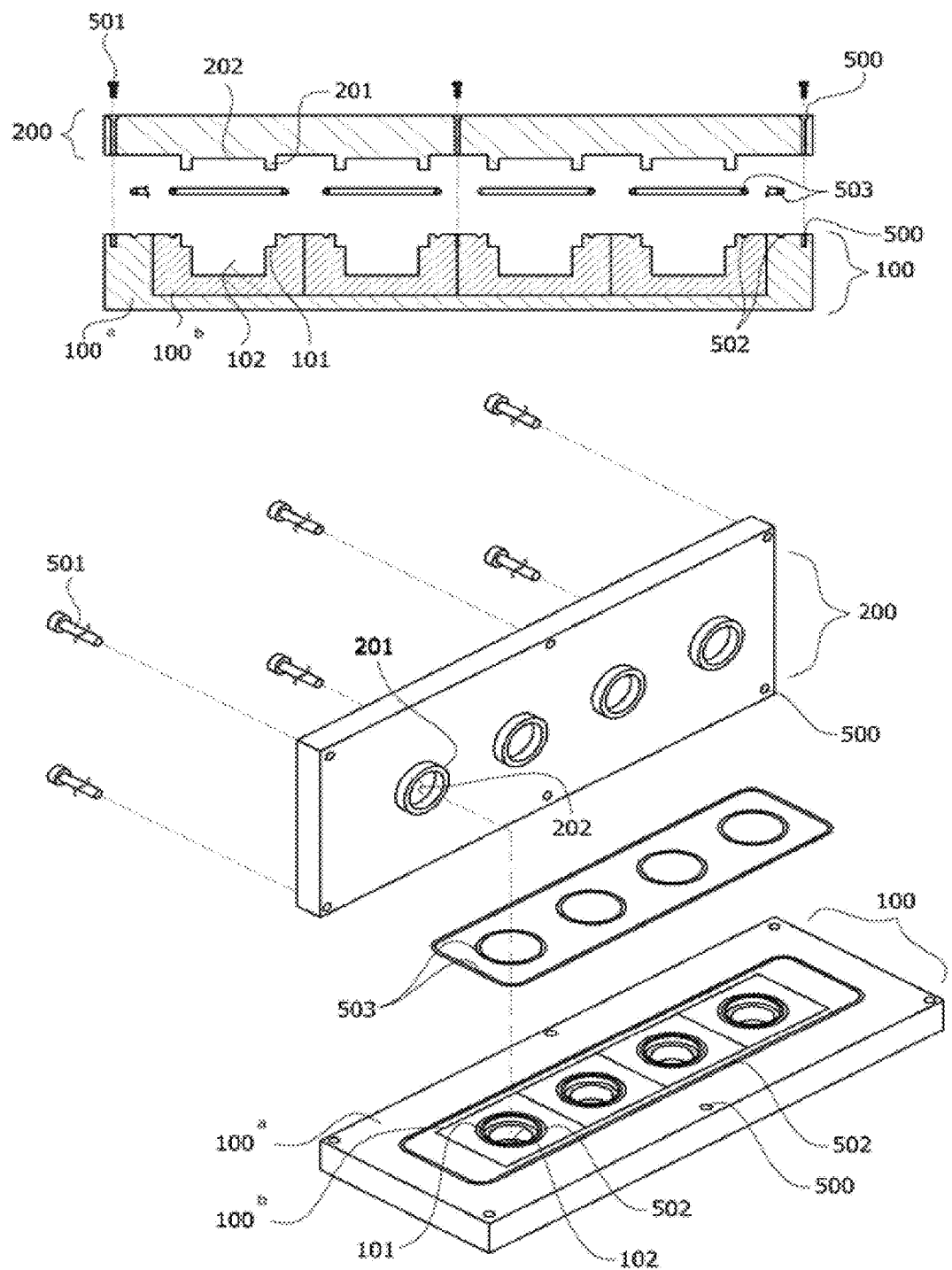

[Fig. 6g]
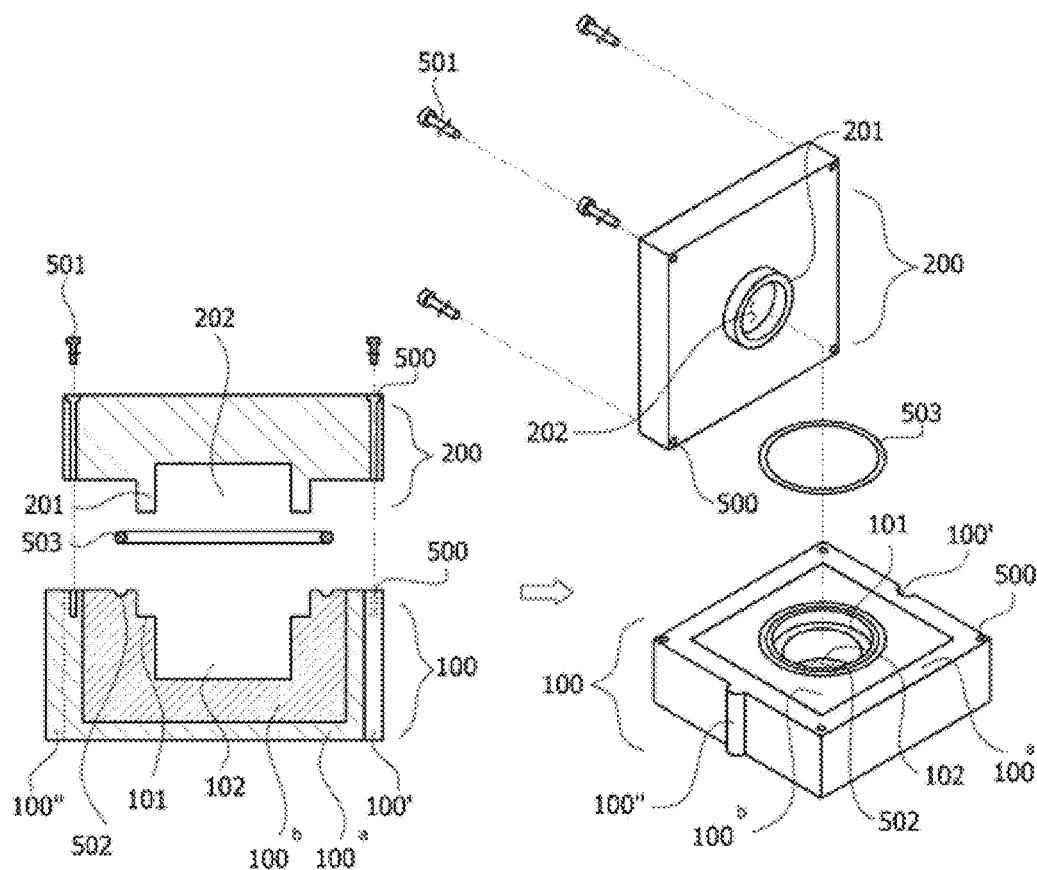

[Fig. 7a]
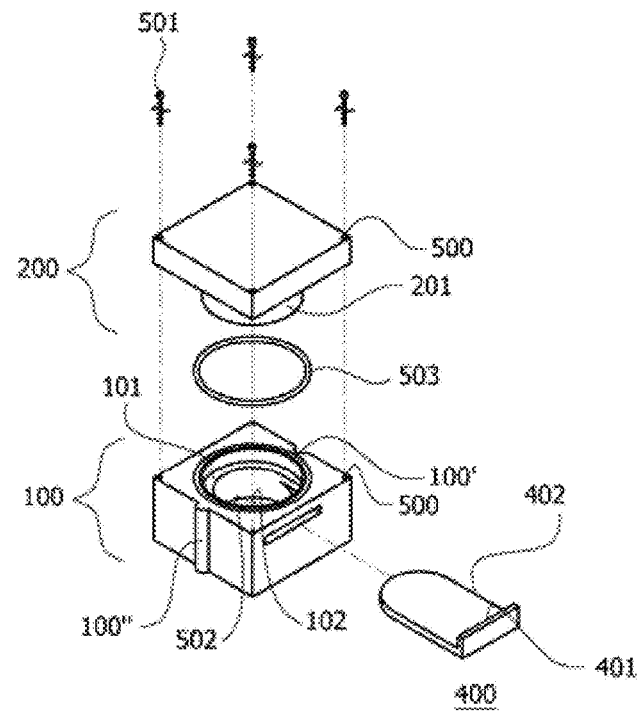
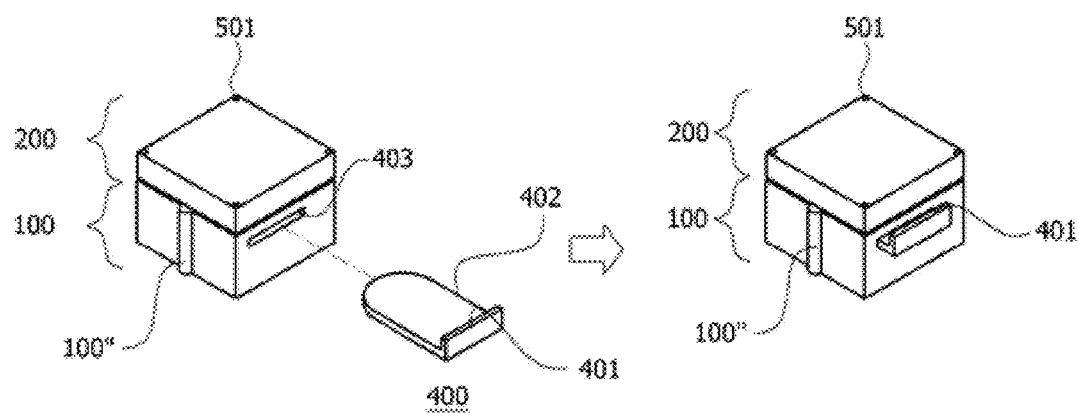

[Fig. 7b]
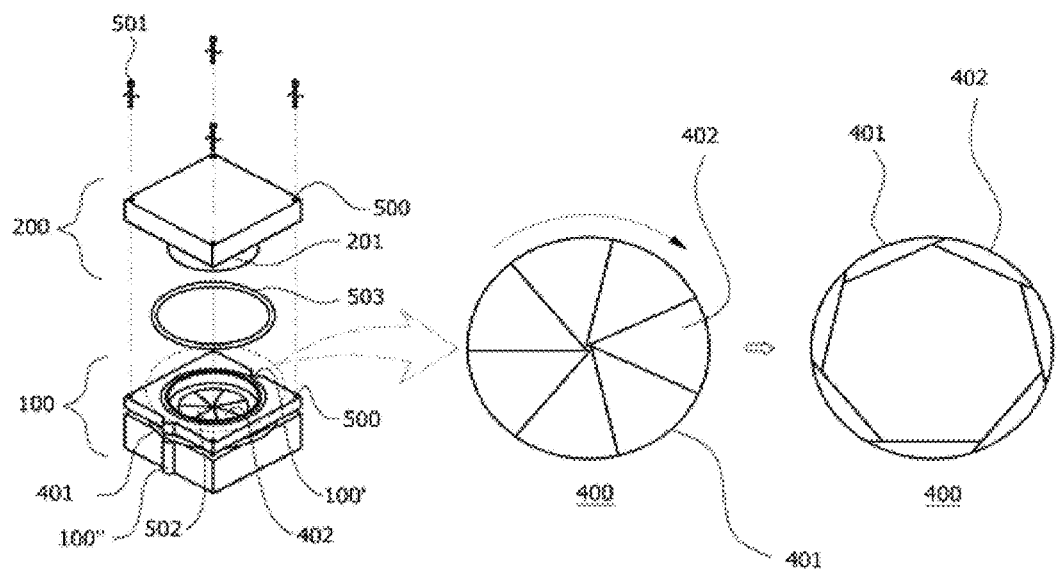
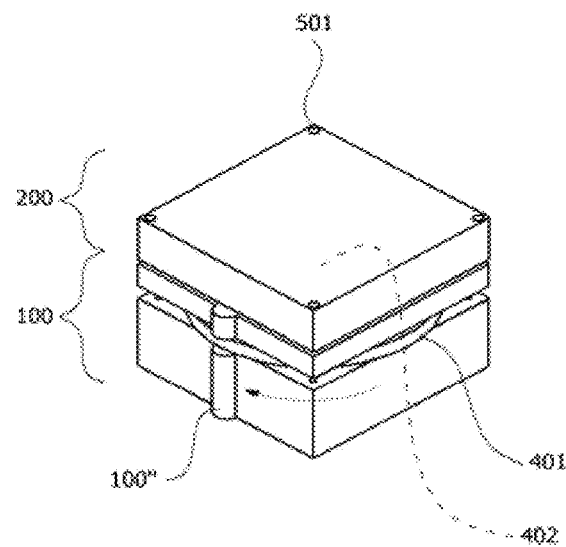

[FIG. 8]
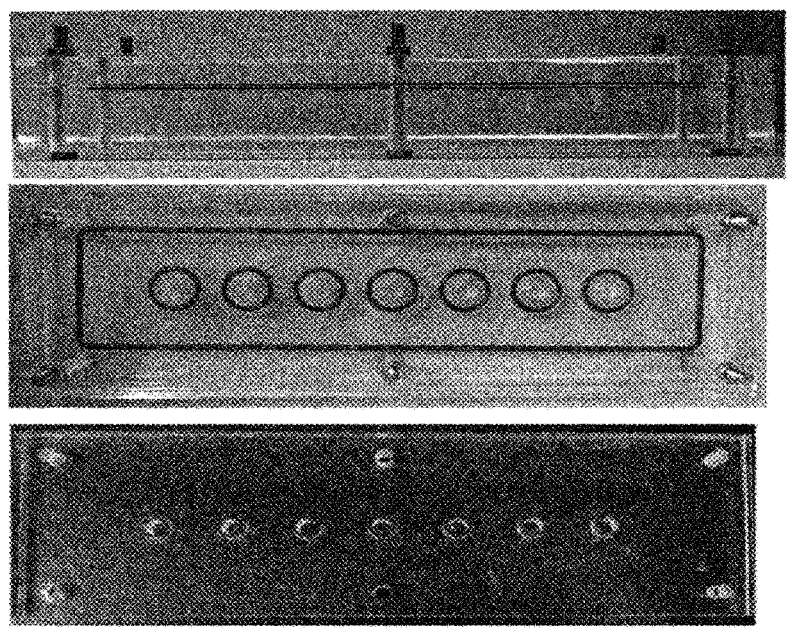
[Fig. 9a]
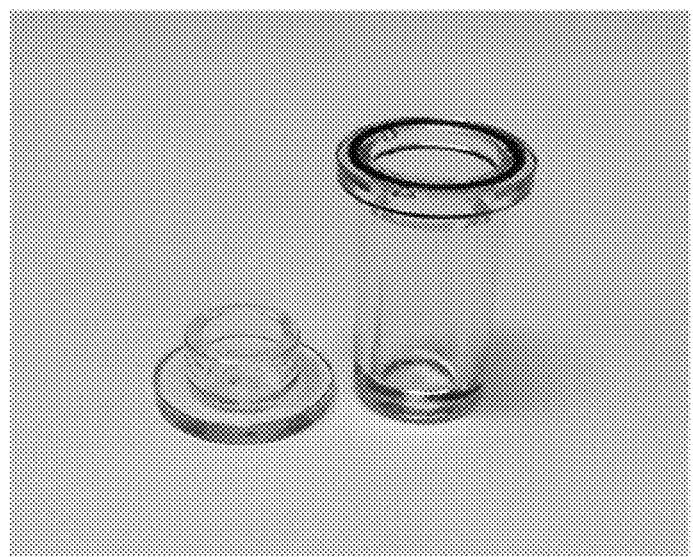

[Fig. 9b]
[Fig. 9c]

[Fig. 10a]
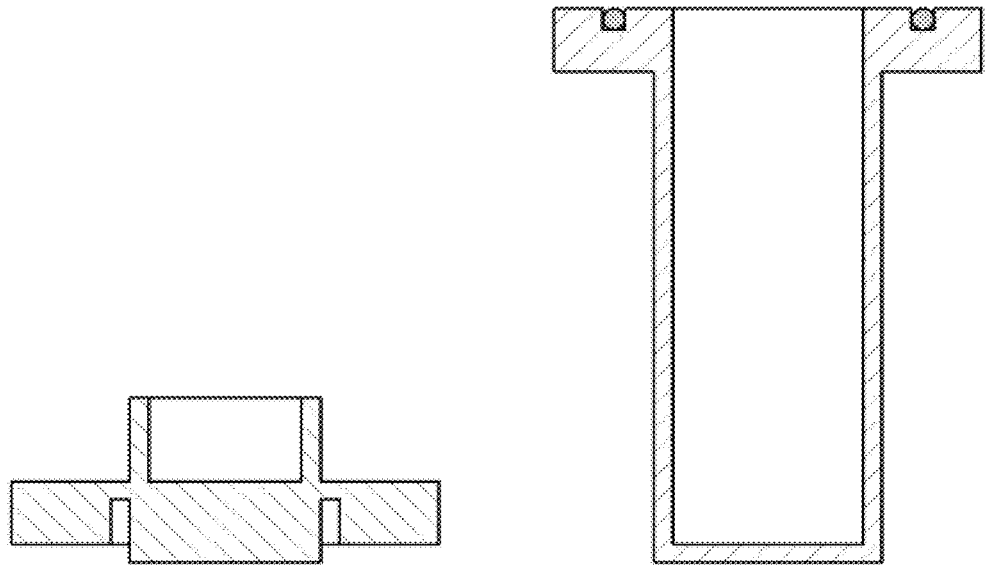
[Fig. 10b]
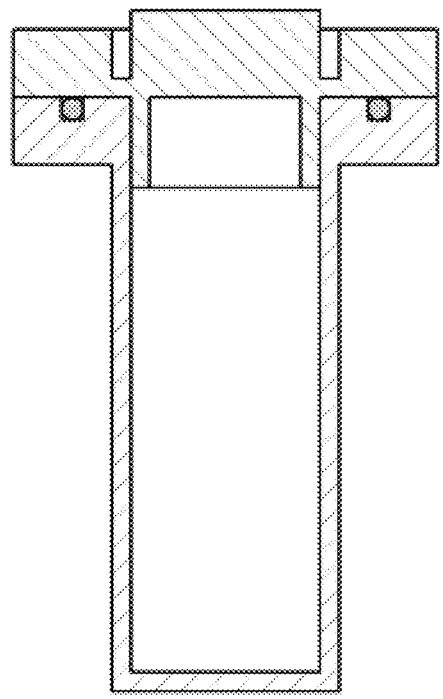

[Fig. 10c]
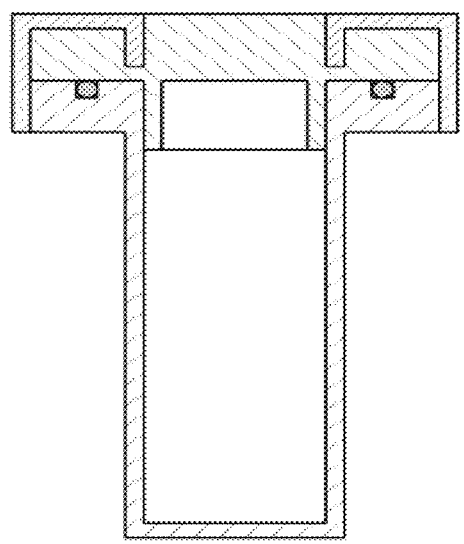
[Fig. 11]
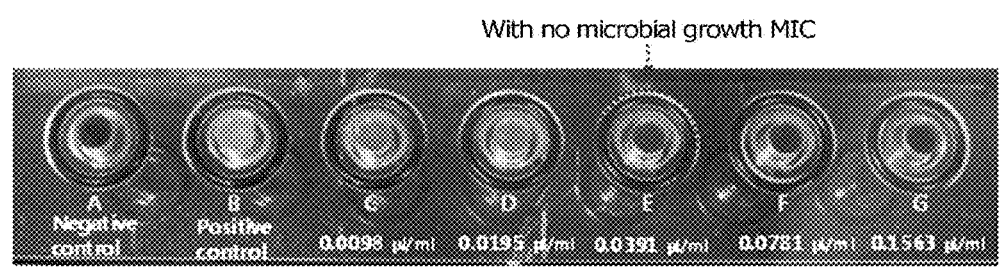

DEVICE FOR MEASURING ANTIMICROBIAL ACTIVITY OF GAS AND METHOD FOR MEASURING ANTIMICROBIAL ACTIVITY OF GAS

CROSS REFERENCE TO RELATED APPLICATION

This application is a U.S. National Phase of International Application No. PCT/KR2015/001127, filed Feb. 4, 2015, which claims priority to South Korean Application No. 10-2014-0029504 filed Mar. 13, 2014, the contents of which are incorporated herein by reference.

TECHNICAL FIELD

The present invention relates to an apparatus for measuring antimicrobial activity of a gas and a method for measuring antimicrobial activity of a gas.

BACKGROUND ART

Recently, technologies for sterilizing food harming microbes (food poisoning or food perishing bacteria) using an antimicrobial gas have been in the limelight. Since antimicrobials in gas phase have superior antimicrobial activities than antimicrobials in liquid phase and do not remain in food, the antimicrobials in gas phase have only a small possibility to harm a human body. Also, there is another advantage in which sensorial changes of foods are very limited. However, since research on antimicrobials in gas phase has been insufficient, a standardized method to evaluate the antimicrobial activity of gas has not been developed yet.

Since no standardized method of measuring antimicrobial activity of a gas has been developed, as a desperate measure, researchers have measured a minimal inhibitory concentration (MIC) and a minimal lethal concentration (MLC) of gas by modifying methods of measuring antimicrobial activities of antimicrobial materials in liquid phase.

Currently, methods of measuring antimicrobial activity of a gas used by researchers have been referred to in various names such as vapor phase diffusion assay (Du et al., 2009), vapor diffusion assay (Nedorostova et al., 2009), disk volatilization method (Tyagi and Malik, 2010), vapor phase assay (Becerril et al., 2007), agar vapor assay (Inouye et al., 2007), etc. In the present invention, FIGS. 1a to 1c illustrate conventional methods of measuring the antimicrobial activities of gases. Here, since standardized experiment conditions are not established in conventional methods, even though the same antimicrobial gas is measured by the same method, a minimal inhibitory concentration is measured to be different depending on the details of the experimental conditions.

For this reason, there is a dire need for a standardized method and apparatus for measuring antimicrobial activity of a gas for reducing microbes.

DISCLOSURE OF INVENTION

Summary of the Invention

Technical Problem

The present invention provides an apparatus for measuring antimicrobial activity of a gas and a method (experimental protocol) for measuring antimicrobial activity of a gas.

Technical Solution

The present inventor performed extensive research to provide an experimental apparatus and standardized experimental protocol for measuring antimicrobial activity of a gas. It was confirmed that, using the developed apparatus and experimental protocol, the growth of microbes can be objectively determined through a color change of a microbe medium and the concentration gradient of antimicrobial gas are not occurred in the apparatus. Therefore, it was concluded that the present invention may be used as a accurate and standardized apparatus and method for measuring antimicrobial activity of a gas.

One aspect of the present invention provides an apparatus for measuring an antimicrobial activity of a gas, including a lower container including a gas generating portion which contains an antimicrobial material and an upper container including a microbe medium portion which accommodates a microbe medium to be in contact with an antimicrobial material in gas phase generated by the gas generating portion.

Another aspect of the present invention provides an experimental protocol to measure an antimicrobial activity of a gas using the apparatus for measuring the antimicrobial activity of the gas described above.

Advantageous Effects

According to embodiments of the present invention, when an apparatus for measuring an antimicrobial activity of a gas is used, a concentration of the gas may be uniformly maintained, and growth of microbes may be objectively checked through a color change in a microbe medium including a pH indicator.

Accordingly, the measuring apparatus according to the present invention may be used as a standardized apparatus for measuring an antimicrobial activity of a gas.

BRIEF DESCRIPTION OF DRAWINGS

FIG. 1 is a mimetic diagram illustrating a conventional method and apparatus for measuring activation of an antimicrobial gas.

FIG. 2a is a mimetic diagram illustrating the principle for measuring a minimal inhibitory concentration of an antimicrobial gas using a measurement apparatus according to the present invention.

FIG. 2b is a mimetic diagram illustrating the principle for measuring a minimal lethal concentration of an antimicrobial gas using the measurement apparatus according to the present invention.

FIGS. 3a to 3g are views illustrating a lower container 100 of an apparatus for measuring antibacterial activity of a gas according to one example of the present invention.

FIGS. 4a to 4c are views illustrating an upper container 200 of the apparatus for measuring antibacterial activity of gas according to one example of the present invention.

FIGS. 5a to 5b are views illustrating an intermediate cover 400 of the apparatus for measuring antibacterial activity of gas according to one example of the present invention.

FIGS. 6a to 6g are views illustrating examples of applying the upper container and the lower container according to one example of the present invention.

FIGS. 7a to 7b are views illustrating examples of applying the intermediate cover according to one example of the present invention.

FIG. 8 is a photo of the apparatus for measuring antibacterial activity of gas according to one example of the present invention.

FIGS. 9 and 10 are photos and views of the upper container and the lower container manufactured as vial shapes according to one example of the present invention.

FIG. 11 is a photo showing a result of measuring a minimal inhibitory dose of Embodiment 1.

DETAILED DESCRIPTION OF THE INVENTION

[Best Mode]

Hereinafter, the present invention will be described in detail with reference to the attached drawings. Throughout the drawings, thicknesses or sizes of components may be exaggerated for clarity and convenience of description. Also, the terms particularly defined considering functions and operations of the present invention may vary according to intentions or practices of users or operators. Accordingly, the definitions of the terms will be given based on the content throughout the specification.

Also, the concept of the present invention is not limited to the provided embodiments, and other embodiments within the range of the same concept may be easily performed by one of ordinary skill in the art and also included in the scope of the present invention.

The present invention relates to an apparatus for measuring antimicrobial activity of a gas that includes a lower container including a gas generating portion containing an antimicrobial material, and an upper container that includes a microbe medium portion accommodating a microbe medium to be in contact with an antimicrobial material in gas phase generated by the gas generating portion.

The lower container of the apparatus for measuring the antimicrobial activity of the gas according to the present invention includes a gas generating portion for containing the antimicrobial material, and the gas generating portion may have a groove shape. One or more of such gas generating portions may be formed. Here, a plurality of such gas generating portions having the same groove shape may be formed with a regular spacing.

The lower container may include a groove and a protrusion on sides. The groove and protrusion are used to easily connect a plurality of such lower containers. The protrusion is formed on one side and the groove is formed on the other side corresponding to the one side for connecting the protrusion of the lower container to a groove of another lower container.

Also, the lower container may further include an external container into which the lower container is inserted. The external container may be formed of a hard material to improve durability of the lower container. The external container may also have a configuration which has a plurality of divided accommodating spaces to allow the lower container to be inserted in each of the external containers.

A groove and a protrusion may be formed on sides of the external container. Here, the groove and the protrusion of the external container may be formed using the same method as that of the lower container described above to connect a plurality of such external containers. When the groove and the protrusion are formed on the external container, the lower container to be inserted in the external container may not include a groove and a protrusion.

Also, a step which is fastened to a fastening protrusion of the upper container which will be described below to couple the lower container with the upper container may be formed on the lower container. The step may effectively seal the lower container and the upper container to maintain an antimicrobial material gas at a constant concentration and to fix the lower container and the upper container at a uniform distance, thereby reducing error caused by a change in the distance between the antimicrobial material and the microbe medium.

Also, a sealing member accommodating groove for preventing the antimicrobial material gas from flowing outward from the container by sealing the lower container and the upper container may be formed at the lower container. The sealing member accommodating groove is included in a sealing portion. In detail, the lower container may include one or more sealing member accommodating grooves for each of the gas generating portions, and a sealing member such as an O-ring may be inserted in the sealing member accommodating groove.

FIG. 3 is a view illustrating a lower container according to one example of the present invention, and the lower container, for example, may have structures $3a$ to $3g$. FIG. 3 illustrates a case in which the lower container has a step 101 and a sealing member accommodating groove 502.

FIG. $3a$ illustrates a case in which the lower container includes one gas generating portion 102, and FIG. $3b$ illustrates a case in which the lower container includes one gas generating portion 102 and is inserted into an external container $100^a$. As shown in FIG. $3b$, when the lower container is inserted into the external container $100^a$, the lower container may be referred to as an internal container $100^b$.

Also, FIG. $3c$ illustrates a case in which the lower container includes one gas generating portion 102, and a protrusion 100" and a groove 100' are formed on sides of the lower container. Also, FIG. $3d$ illustrates a case in which the external container $100^a$, includes the protrusion 100" and the groove 100' are formed on sides of the external container. As shown in FIG. $3d$, when the external container $100^a$ is formed, the internal container $100^b$ may not include the protrusion 100" and the groove 100'. Also, in the drawings described above, although it is shown that a groove or a protrusion is formed on one side and the other side corresponding to the one side, there may be provided a configuration in which a groove may be formed on two connected sides and a protrusion may be formed on two other sides.

Also, FIGS. $3e$ to $3g$ illustrate cases in which one or more gas generating portions are formed. As shown in FIG. $3e$, the lower container 100 may have a structure in which a plurality of such gas generating portions 102 are formed, or, although not shown in the drawings, a structure in which a plurality of such lower containers 100, each of which includes one gas generating portion 102, may be connected. Here, the lower container may have a structure in which a protrusion and a groove area formed on one side and the other side in such a way that a protrusion of one lower container may be coupled with a groove of another lower container. Also, as shown in FIG. $3f$, there may be provided a structure in which the plurality of lower containers 100 (internal containers $100^b$) including one gas generating portion 102 are connected and the connected internal containers $100^b$ are inserted in the external container $100^a$. As shown in FIG. $3g$, the external container $100^a$ may include a plurality of divided accommodating spaces and may have a structure in which the lower container including the gas generating portion, that is, the internal container $100^b$ is inserted into each of the accommodating spaces of the external container $100^a$.

The lower container described above, that is, in the gas generating portion of the lower container, an antimicrobial material is accommodated.

The antimicrobial material is not particularly limited and may be any material capable of generating an antimicrobial gas which can suppress or destroy growth and development of all bacteria to be controlled including bacteria harmful to a human body, food putrefactive bacteria, zymogens, etc.

In detail, the antimicrobial may be an antimicrobial gas or a volatile antimicrobial material. The type of the antimicrobial gas is not particularly limited and may be one or more selected from the group consisting of sulfur dioxide ($SO_2$), ozone gas, carbon dioxide ($CO_2$), nitric oxide (NO), and hydrogen sulfide ($H_2S$). The volatile antimicrobial material may be essential oils, a volatile organic material, or a volatile inorganic material. The essential oils may be one or more selected from the group consisting of cinnamon, lemon, garlic, lemongrass, cypress, pine, black pepper, sage, cistus, citronella, clary sage, Spanish thyme, tea tree, spearmint, clove, thyme linalool, oregano, peppermint, and thyme thymol. The volatile organic material may be one or more selected from the group consisting of acetic acid, sodium lactate, sorbic acid, benzoic acid, triclosan, ethanol, and ethyl acetate. The volatile inorganic material may be one or more selected from the group consisting of chlorine dioxide and hydrogen peroxide.

The apparatus for measuring the antimicrobial activity of the gas according to the present invention includes an upper container, and the upper container is located above a lower container. The upper container includes a microbe medium portion. A microbial medium is accommodated in the microbe medium portion and is in contact with an antimicrobial material in gas phase generated in a gas generating portion of the lower container described above. Also, a fastening protrusion may be formed on the upper container and may be fastened to a step of the lower container.

In detail, the microbe medium portion of the upper container may be formed on an inner surface of the fastening protrusion.

The structure of the upper container is not particularly limited and may be any one capable of being fastened to the lower container and may vary according to a structure of the lower container. In detail, the number of the microbe medium portions may be determined according to the number of the gas generating portions of the lower container.

Also, the upper container may include a groove and a protrusion on sides. The groove and protrusion are used to easily connect a plurality of such upper containers. The protrusion is formed on one side and the groove is formed on the other side corresponding to the one side to connect the protrusion of the upper container to a groove of another upper container. Particularly, when a groove and the protrusion are formed on the sides of the upper container, the lower container may also include the groove and the protrusion, and the grooves and the protrusions of the upper container and the lower container may be formed to be connected to each other.

FIG. 4 is a view illustrating an upper container according to one example of the present invention, and the upper container, for example, may have structures 4a to 4c. In FIG. 4, the upper container includes a fastening protrusion 201 and a microbe medium portion 202.

FIG. 4a illustrates a case in which one microbe medium portion 202 is provided. FIGS. 4b and 4c illustrate cases in which a plurality of such microbe medium portions 202 is provided. Particularly, FIG. 4c illustrates a structure in which a groove and a protrusion are formed on sides of the upper container.

A microbe medium of the microbe medium portion of the upper container according to the present invention may include a high-nutrient medium, microbes, and a pH indicator.

The high-nutrient medium is a medium including a nutritive material necessary for growth and development of microbes. The nutritive material may be one or more monosaccharides selected from the group consisting of glucose, L-arabinose, fructose, D-xylose, D-mannose, galactose, D-trehalose, cellobiose, M-mannitol, glycerin, inositol, sorbitol, L-rhamnose, etc.

The amount of the nutritive material is not particularly limited and, for example, may include from 0.01 to 3 weight percent in comparison with 100 weight percent of the high-nutrient medium.

All microbes to be controlled such as bacteria harmful to a human body, food putrefactive bacteria, zymogens, etc. may be used as the microbes. For example, the microbes may be food poisoning bacteria such as *Escherichia coli* (O157:H7) or *Listeria monocytogenes*, mold such as *Aspergillus flavus*, and yeast such as *Saccharomyces Cerevisiae*, etc. but is not limited thereto.

The microbes may be included to a degree which allows a change in color of the microbe medium to be well shown according to an increase thereof on the medium. Although not limited thereto, for example, the concentration of the microbes may be from $10^5$ to $10^7$ cfu/ml. When it is inoculated with the microbes less than $10^5$ cfu/ml, it is apprehensible that the change in color of the medium does not easily occur. When it is inoculated with the microbes more than $10^7$ cfu/ml, it is apprehensible that a low antimicrobial activity of an antimicrobial material is measured.

Also, the pH indicator is used to check a change in pH caused by secretions discharged during a process in which the microbes proliferate and is not particularly limited as long as the change of pH can be checked. Generally, pH of the high-nutrient medium is 7.0 and pH of the medium after the microbes proliferate is from 4.0 to 6.8. Accordingly, the pH indicator used in the present invention may have a discoloration range at pH 6.8 or less. For example, the pH indicator may be any one selected from the group consisting of bromocresol purple, bromocresol green, bromophenol blue, phenol red, alizarin yellow R, cresol red, and neutral red, and more particularly, may be bromocresol purple.

The pH indicator may be included at from 0.005 to 0.2 weight percent, from 0.005 to 0.1 weight percent, from 0.005 to 0.05 weight percent, from 0.01 to 0.05 weight percent, or from 0.02 to 0.03 weight percent in comparison with 100 weight percent of the high-nutrient medium. When the pH indicator within the range described above is included, the concentration of the antimicrobial material of the medium on which the microbes do not grow is thereby easily checked by the change in the color of the medium that depends on whether the microbes proliferate. In detail, when the pH indicator is included at less than 0.005 weight percent, it is apprehensible that color development of the medium is weak. When the pH indicator is more than 0.2 weight percent, it is apprehensible that growth and development of the microbes may be suppressed or observing a change in the color development of the medium on which the microbes proliferate may not be easy.

That is, the apparatus for measuring the antimicrobial activity of the gas according to the present invention may allow the growth and development of the microbes to be objectively checked through the change in color of the microbe medium using the pH indicator added in the microbe medium.

The apparatus for measuring the antimicrobial activity of the gas according to the present invention may further include a fixing portion which connects and fixes the lower container and the upper container to more strongly connect the lower container and the upper container.

The fixing portion is not particularly limited as long as the lower container and the upper container can be connected and fixed. For example, a screw, a clip, or a cicada chain may be used, and in detail, a screw may be used.

The fixing portion is shown in FIGS. 3 and 4. As shown in FIGS. 3 and 4, the fixing portion includes a screw hole 500. The screw hole 500 may be formed to penetrate the upper container and the lower container. And a screw, etc. may be positioned at the screw hole 500 to fix and couple the upper container and the lower container.

Meanwhile, FIGS. 6a to 6g are views illustrating examples of applying the lower container and the upper container described above. In detail, FIGS. 6a to 6g illustrate a case of using the upper container 200 corresponding to the lower container 100 shown in FIGS. 3a to 3g.

In FIG. 6, the upper container 200 with the lower container 100 by positioning a screw 501 in the screw hole 500 to couple and airtightness is improved by accommodating a sealing member 503 in the sealing member accommodating groove 502.

Meanwhile, the apparatus for measuring the antimicrobial activity of the gas according to the present invention may further include an intermediate cover which seals a gas generating portion of the lower container, in addition to the upper container and the lower container described above. The intermediate cover allows a saturated gas generated by an antimicrobial material to exist in a limited space, thereby allowing the gas at a constant concentration to be in contact with microbes. Also, when a plurality of such gas generating portions are used, the intermediate cover is used to allow contact durations between the microbe medium and gas of the antimicrobial material at each of the gas generating portions to be identical, thereby making a more accurate measurement of the antimicrobial activity of the gas possible.

The intermediate cover may have a configuration of being detachably inserted through a through hole formed on one side of the lower container.

In detail, the intermediate cover may include an adjusting portion and a hiding portion. The adjusting portion may function as a handle for easily attaching or detaching the intermediate cover to or from the through hole of the lower container, and opening and closing of the gas generating portion may be externally adjusted by the adjusting portion. Also, the hiding portion may be inserted in the gas generating portion of the lower container through the through hole and may prevent the gas of the antimicrobial material from being in contact with the microbe medium by blocking the gas generating portion. Preferably, the intermediate cover may include a through hole to allow the step portion of the lower container to pass.

FIGS. 7a and 7b are views of the apparatus including an intermediate cover 400 according to the present invention.

The lower container 100 may include a through hole 403 on one side, and the intermediate cover 400 may be detachably inserted through the through hole 403.

In FIGS. 7a and 7b, the intermediate cover 400 includes an adjusting portion 401, a hiding portion 402, and the through hole 403. The intermediate cover 400 may be inserted in the gas generating portion through the step 101 of the lower container 100, and opening and closing of the gas generating portion 102 of the lower container 100 may be externally adjusted by the adjusting portion 401.

The intermediate cover 400 may have a flat shape as shown in FIG. 5a or may have the shape of an aperture of a camera as shown in FIG. 5b.

FIG. 8 is a photo of the apparatus for measuring the antimicrobial activity of the gas according to the present invention. Here, the apparatus includes the lower container including a plurality of microbe medium portions.

Also, in the present invention, FIGS. 9 and 10 are photos and views illustrating an upper container and a lower container according to one example of the present invention. Here, the upper container and the lower container may be manufactured in vial shapes. FIGS. 9a and 10a are a photo and a view separately illustrating the upper container and the lower container. FIGS. 9b and 10b illustrate a state in which the upper container and the lower container are coupled. FIGS. 9c and 10c illustrate a state of coupling and sealing the upper container and the lower container to make them airtight. Here, silver septa may be used for sealing.

In the present invention, the apparatus for measuring the antimicrobial activity of the gas is manufactured in the vial shape to be easily portable and one or more vials are fixed to an additional supporting body to perform various experiments such as a minimal inhibitory concentration test, etc.

Also, the present invention relates to a method of measuring an antimicrobial activity of a gas using the apparatus for measuring the antimicrobial activity of the gas described above.

The method of measuring the antimicrobial activity of the gas may include containing an antimicrobial material in the gas generating portion of the apparatus for measuring the antimicrobial activity of the gas, adsorbing the microbe medium which includes a high-nutrient medium, a pH indicator and microbes to the upper container, fixing and sealing the lower container and the upper container to culture, and checking the color of the microbe medium.

In the present invention, the lower container may include the plurality of gas generating portions, and the antimicrobial material at a different concentration may be injected into each of the gas generating portions.

The antimicrobial activity of the gas may be determined by measuring a minimal inhibitory concentration (MIC) or a minimal lethal concentration (MLC) of the gas.

The MIC means a minimal concentration for suppressing growth and development of a certain microbe, which is also referred to as a minimal inhibitory concentration. The MIC may be known by checking a minimal concentration of the antimicrobial material at a point in time that the microbe medium is discolored.

In the present invention, FIG. 2a is a view illustrating a method of measuring the MIC according to one exemplary example.

As shown in FIG. 2a, the antimicrobial material at various concentrations is added to the plurality of gas generating portions, and the gas of the antimicrobial material comes in contact with the microbe medium, thereby confirming a minimal concentration of the antimicrobial material at which the growth and development of the microbes are suppressed through a change in color of the medium.

Also, the MLC means a minimal concentration for destroying a certain microbe. The MLC may be known by confirming a concentration of the antimicrobial material on the medium at which microbes do not grow when a surface of the microbe medium which does not change in color is collected, streaked on a nutrient agar to be cultured, and microbes do not grow.

In the present invention, FIG. 2b is a view illustrating a method of measuring the MLC according to one exemplary example.

As shown in FIG. 2b, the MLC may be measured by collecting a surface of a medium which does not change in color and streaking a nutrient agar.

The method of measuring the antimicrobial material of the gas according to the present invention has a feature of objectively confirming the growth and development of microbes through the change in color of the microbe medium including the pH indicator. This is differentiated from the conventional method of measuring an antimicrobial activity of a gas in which it is necessary to subjectively determine growth and development of microbes through a change in size of an inhibitory zone or a change in size of a microbe colony (cluster) on a surface on which microbes are applied. Also, there is a feature of measuring antimicrobial activities of the antimicrobial material at various concentrations at the same time by providing a plurality of lower containers and a plurality of upper containers. Accordingly, the method of measuring the antimicrobial activity of the gas according to the present invention may be used as a standardized method of measuring an antimicrobial activity of a gas.

[Mode for Invention]

Advantages, features, and a method of achieving the same will be specified with reference to the embodiments described below in detail together. However, the present invention will not be limited to the embodiments described below and may be embodied in various different forms. The exemplary embodiments are merely provided to completely disclose the present invention and to allow one of ordinary skill in the art to fully understand the present invention. The present invention is defined by the scope of claims.

Manufacture Example 1

Application of a Microbe Medium to a Measuring Apparatus 0.025% of bromocresol purple which is a pH indicator was added to a high-nutrient medium to which 1% of glucose has been added. 350 ul of the medium in liquid form was put in an upper container and cured and then 10 ul of a microbe suspension ($10^7$ cfu/ml) was injected and then kept at room temperature for 30 minutes to allow microbes to be adsorbed to the medium.

When microbes proliferate on this medium, 1% of the added glucose ferments and generates lactic acid. When the lactic acid is generated, the lactic acid reacts with bromocresol purple which is the pH indicator added to the medium and shows yellow color. Meanwhile, when microbes do not grow, purple which is the color of bromocresol purple is shown. That is, it may be determined by checking the color of the medium whether microbes grow or not.

Embodiment 1

Measurement of MIC of Cinnamon Bark Essential Oil with Respect to *E. coli* O157:H7

*Escherichia coli* O157:H7 which is enterohemorrhagic *Escherichia coli* was used as microbes, and various essential oils were used for generating a gas of an antimicrobial material. Cinnamon was used as essential oil.

A is a negative comparative sample, and *Escherichia coli* O157:H7 and essential oil were not added. B is a positive comparative sample, and *Escherichia coli* O157:H7 was added but essential oil was not added. In the cases of C, D, E, F, and G, *Escherichia coli* O157:H7 was added and 0.0098 ul/ml, 0.0195 ul/ml, 0.0391 ul/ml, 0.0781 ul/ml, and 0.1563 ul/ml of essential oils were added.

In the embodiment of the present invention, the apparatus manufactured as shown in FIG. 8 was used.

In detail, the upper container and the lower container were fixed using the fixing portion, and they were cultured at a temperature of 30° C. for 48 hours. After finishing the culture, a minimal inhibitory concentration was determined by confirming the color of the medium of the upper container.

FIG. 11 is a photo illustrating a result of measuring the minimal inhibitory concentration of a cinnamon essential oil according to the method described above.

As shown in FIG. 11, since colors of E, F, and G were purple, it is apparent that microbes did not grow, and E with a lowest concentration of cinnamon indicates the minimal inhibitory concentration. Accordingly, it may be checked that the minimal inhibitory concentration of cinnamon with respect to *E. coli* O157:H7 is 0.0391 ul/ml.

Embodiment 2

Method of Measuring MLC of Cinnamon Bark Essential Oil with Respect to *E. coli* O157:H7

Surface samples of the media E, F, and G whose color was purple and on which *E. coli* O157:H7 did not grow in Embodiment 1 described above were streaked on nutrient agars using a loop and cultured at a temperature of 30° C. for 24 hours. After the culture, the amount of essential oil applied to G was determined to be the MLC, for which a streaked sample on nutrient agar did not grow.

As a result, it may be confirmed that the MLC of cinnamon with respect to *E. coli* O157:H7 is 0.1563 ul/ml.

Embodiment 3

Result of Measuring MIC and MLC of Various Natural Antimicrobial Gases with Respect to *E. coli* O157:H7

The MIC and MLC of essential oils in following Table 1 were measured using the same methods as shown in Embodiments 1 and 2 described above.

TABLE 1

| Essential oils | MIC (ul/ml) | MLC (ul/ml) |
| --- | --- | --- |
| Lemon | 20.00 | >20.00 |
| Garlic | 10.00 | 10.00 |
| Lemongrass | 2.50 | 2.50 |
| Cypress | 2.50 | 2.50 |
| Pine | 2.50 | 2.50 |
| Black pepper | 1.25 | 2.50 |
| Sage | 1.25 | 1.25 |
| Cistus | 1.25 | 1.25 |
| Citronella | 1.25 | 1.25 |
| Clary sage | 1.25 | 2.50 |
| Spanish thyme | 1.25 | 1.25 |
| Tea tree | 1.25 | 1.25 |
| Spearmint | 0.6250 | 1.25 |
| Clove | 0.6250 | 1.25 |
| Thyme linalool | 0.6250 | 0.6250 |
| Oregano | 0.3125 | 0.3125 |
| Peppermint | 0.3125 | 0.6250 |
| Thyme thymol | 0.0781 | 0.0781 |
| Cinnamon | 0.0391 | 0.1563 |

DESCRIPTION OF REFERENCE NUMERALS

100: Lower container, 101: Step, 102: Gas generating portion, 100$^a$: External container, 100$^b$: Internal container
200: Upper container, 201: Fastening protrusion, 202: Microbe medium portion
100': Groove, 100": Protrusion
400: Intermediate cover, 401: Adjusting portion, 402: Hiding portion, 403: Through hole
500: Screw hole, 501: Screw, 502: Sealing member accommodating groove, 503: Sealing member

INDUSTRIAL APPLICABILITY

When an apparatus for measuring an antimicrobial activity of a gas according to the present invention is used, a concentration of the gas may be constantly maintained, and growth and development of microbes may be objectively confirmed using a color change in a microbe medium including a pH indicator.

Accordingly, the measuring apparatus according to the present invention may be used as a standardized apparatus for measuring antimicrobial activity of a gas.

The invention claimed is:

1. An apparatus for measuring an antimicrobial activity of a gas, comprising:
    a lower container comprising a gas generating portion which contains an antimicrobial material; and
    an upper container comprising a microbe medium portion which accommodates a microbe medium to be in contact with an antimicrobial material in gas form generated by the gas generating portion,
    wherein the lower container comprises a protrusion formed on one side and a groove formed on the other side corresponding to the one side.

2. The apparatus of claim 1, wherein the lower container comprises one or more gas generating portions.

3. The apparatus of claim 1, wherein the lower container further comprises an external container into which one or more lower containers comprising the gas generation portions are inserted.

4. The apparatus of claim 3, wherein the external container comprises a protrusion formed on one side and a groove formed on the other side corresponding to the one side.

5. The apparatus of claim 3, wherein the external container has a plurality of divided accommodating spaces, and the one or more lower containers comprising the gas generating portion are inserted into each of the accommodating spaces.

6. The apparatus of claim 1, wherein a step is formed on an inside surface of the lower container, and the step is fastened to a fastening protrusion formed on the upper container.

7. The apparatus of claim 1, further comprising a sealing portion formed on a surface of the lower container in contact with the upper container,
    wherein the sealing portion is comprising a sealing member accommodating groove.

8. The apparatus of claim 1, wherein the upper container comprises one or more microbe medium portions.

9. The apparatus of claim 1, wherein the upper container comprises a protrusion formed on one side and a groove formed on the other side corresponding to the one side.

10. The apparatus of claim 1, further comprising an intermediate cover which seals the gas generating portion,
    wherein the intermediate cover is detachably inserted through a through hole formed in one side of the lower container.

11. The apparatus of claim 1, wherein the antimicrobial material contained in the gas generating portion is one of an antimicrobial gas and a volatile antimicrobial material.

12. The apparatus of claim 1, wherein a microbe medium accommodated in the microbe medium portion is a color-developed medium which comprises a high-nutrient medium, a pH indicator, and microbes,
    wherein the high-nutrient medium comprises nutritive materials, and the nutritive materials comprises 0.01 to 3 weight percent in comparison with 100 weight percent of the high-nutrient medium.

13. The apparatus of claim 12, wherein the high-nutrient medium comprises one or more selected from nutritive materials consisting of glucose, L-arabinose, fructose, D-xylose, D-mannose, galactose, D-trehalose, cellobiose, M-mannitol, glycerin, inositol, sorbitol, and L-rhamnose.

14. The apparatus of claim 12, wherein the pH indicator is any one selected from the group consisting of bromocresol purple, bromocresol green, bromocresol blue, methyl red, bromothymol blue, phenol red, alizarin yellow R, cresol red, and neutral red.

15. The apparatus of claim 12, wherein microbes are selected from the group consisting of bacteria, mold, and yeast.

16. A method of measuring an antimicrobial activity of a gas, comprising:
    containing an antimicrobial material in a gas generating portion of the apparatus for measuring the antimicrobial activity of the gas according to claim 1;
    adsorbing a microbe medium which comprises a pH indicator and microbes to an upper container;
    fixing and sealing a lower container and the upper container and then culturing; and
    confirming a color of the microbe medium.

17. The method of claim 16, wherein the lower container comprises a plurality of gas generating portions, and each of the gas generating portions contains an antimicrobial material with a different concentration.

18. The method of claim 17, wherein a minimal inhibitory concentration is confirmed by confirming the minimum concentration of the antimicrobial material in the microbe medium which causes the microbe medium not to change in color.

19. The method of claim 18, wherein a minimal lethal concentration is checked by collecting a surface of the microbe medium which has not changed in color, streaking a nutrient agar for culture, and confirming the minimum concentration of the antimicrobial material in the microbe medium at which microbes do not grow.

* * * * *